United States Patent [19]

Stjernschantz et al.

[11] Patent Number: 5,114,971
[45] Date of Patent: May 19, 1992

[54] PROSTAGLANDIN DERIVATIVES FOR THE TREATMENT OF GLAUCOMA OR OCULAR HYPERTENSION

[75] Inventors: Johan W. Stjernschantz; Bahram Resul, both of Uppsala, Sweden

[73] Assignee: Kabi Pharmacia AB, Uppsala, Sweden

[21] Appl. No.: 601,383

[22] Filed: Oct. 23, 1990

Related U.S. Application Data

[63] Continuation of Ser. No. 375,018, May 15, 1989, abandoned.

[51] Int. Cl.⁵ .................................................. A61K 31/557
[52] U.S. Cl. ................................................................ 514/530
[58] Field of Search ..................................................... 514/530

[56] References Cited

U.S. PATENT DOCUMENTS 4,599,353  7/1986  Bito ........................................ 514/530

Primary Examiner—Robert Gerstl
Attorney, Agent, or Firm—Fred Philpitt

[57] ABSTRACT

11-epi $PGF_2$ alpha esters are employed in treating glaucoma or ocular hypertension.

12 Claims, No Drawings

PROSTAGLANDIN DERIVATIVES FOR THE TREATMENT OF GLAUCOMA OR OCULAR HYPERTENSION

This is a continuation of application Ser. No. 375,018, filed May 15, 1989 now abandoned and the benefits of 35 USC 120 are claimed relative to it.

The invention is concerned with the use of derivatives of a specific diastereomer of prostaglandin $F_{2alpha}$, viz. 11 epi, for the treatment of glaucoma or ocular hypertension. The invention furthermore also relates to ophthalmological compositions containing an active amount of these prostaglandin derivatives.

Glaucoma is an ocular disorder characterized by elevated intraocular pressure, excavation of the optic nerve head and gradual loss of the vision field. An abnormally high intraocular pressure will have a generally detrimental effect on the eye; and there are clear indications that this is probably the main factor causing degenerative changes of the retina in glaucoma patients. However, the pathophysiological mechanism underlying open-angle glaucoma is still unknown. If not treated successfully the disease will usually proceed to blindness sooner or later, its course towards that stage being characterized by a slow but progressive loss of vision.

The intraocular pressur IOP (abbr. of intraocular pressure) is usually defined by the formula $$IOP = P_e - F \cdot R \qquad (1)$$

where $P_e$ is the pressure in the episcleral veins, generally considered to be around 9 mm Hg; F is a measure of aqueous humor flow rate; and R is the resistance to aqueous humor outflow through the trabecular meshwork and adjacent tissue into Schlemm's canal.

Another path along which the aqueous humor may flow, in addition to the Schlemm's canal path, is via the ciliary muscle into the suprachoroidal space and then out of the eye through the sclera. This uveoscleral path has been described by e.g. Bill (1975). The pressure gradient along this path is very insignificant as compared to the gradient in the first mentioned case over the interior wall of Schlemm's canal and adjacent tissue. The flow-limiting step along the uveoscleral path is believed to reside in the flow from the anterior chamber into the suprachoroidal space.

A more complete formula is the following:

$$IOP = P_e + (F_t - F_u) \times R \qquad (2)$$

where $P_e$ and R have the same meanings as above; $F_t$ represents the total outflow of aqueous humor; and $F_u$ represents that portion thereof which goes via the uveoscleral path.

In humans the IOP will normally be within the range of from 12 to 22 mm Hg. At higher values, e.g. exceeding 22 mm Hg, there is a risk that the eye may be affected. In a special form of glaucoma, the so-called low-tension glaucoma, lesions will occur at intraocular pressure levels which are generally regarded as physiological. Possibly this may be due to an increased pressure sensitivity of the eye of such an individual. Also the opposite type of phenomenon is known, i.e. some individuals may have an abnormally high intraocular pressure without any noticeable distinct defects in their vision field or optic nerve head. Such conditions are usually named "ocular hypertension".

Glaucoma treatments may be given by means of drugs, laser or surgery. In the case of drug treatments, the purpose is to achieve a reduction of either the flow (F) or the resistance (R), which will result in a lower IOP according to formula (1) above; or alternatively the purpose may be to increase the flow via the uveoscleral path—which too will be a means of lowering the pressure as can be seen from formula (2). Cholinergic agonists like for instance pilocarpine reduce the intraocular pressure mainly by increasing the outflow through Schlemm's canal.

Interest in prostaglandins as IOP-reducing substances has been growing substantially for quite some time; the mechanism underlying their effect probably being an increased uveoscleral outflow (Crawford et al. 1987, and Nilsson et al. 1987). These substances on the other hand do not appear to have any effect on either the formation of aqueous humor or the conventional outflow through Schlemm's canal (Crawford et al. 1987).

The use of prostaglandins and derivatives thereof is described in for example U.S. Pat. No. 4,599,353 and EP 87103714.9.

With respect to the practical usefulness of some of the previously described prostaglandins and derivatives as suitable as drugs for treating glaucoma or ocular hypertension, a limiting factor is their property of causing superficial irritation and vasodilatation in the conjunctiva. It is probable moreover that prostaglandins have an irritant effect on the sensory nerves of the cornea. Thus local side effects will arise in the eye already when the amounts of prostaglandin administered are quite small—that is, already when the doses are lower than those that would be desirable for achieving maximum pressure reduction. It has thus been found for instance that for this reason it is clinically impossible to use $PGF_{2alpha}$-1-isopropyl ester in the amount that would give maximum pressure reduction. Prostaglandins being naturally occurring autacoids are very potent pharmacologically and affect both sensory nerves and smooth muscle of the blood vessels. Since the effects caused by administrations of $PGF_{2alpha}$ and its esters to the eye comprise in addition to pressure reduction also irritation and hyperemia (increased blood flow) the doses currently practicable in clinical tests are necessarily very low. The irritation experienced when $PGF_{2alpha}$ or its esters are applied consists mainly in a feeling of grittiness or of having a foreign body in one's eye, this being usually accompanied by increased lacrimation.

We have now found, surprisingly, that a diastereomer of prostaglandin $PGF_{2alpha}$, viz. 11 epi, will lower the eye pressure without causing any substantial irritation. In this stereoisomer the hydroxyl at carbon atom 11 lies above the cyclopentane ring. This isomer of $PGF_{2alpha}$ has been known heretofore; it is a metabolite of $PGD_2$ (Liston and Roberts 1985, Pugliese et al. 1985). The 11 epi $PGF_{2alpha}$-1-isopropyl ester which as far as we know has not been described heretofore will give rise to hyperemia in the conjunctiva to about the same extent as the $PGF_{2alpha}$-1-isopropyl ester, but this will not involve any hazard or inconvenience as long as irritation problems are absent.

The present invention thus relates to 1-alkyl or 1-alkylaryl esters of 11 epi $PGF_{2alpha}$ to be used for treating glaucoma or ocular hypertension. The alkyl chain of the 1-alkyl esters comprises 1-10, preferably 1-7, and especially 1-5 carbon atoms. The 1-alkylaryl esters have an aryl group monosubstituted by a lower alkyl chain. This lower alkyl chain has 1-5 carbon atoms. In an embodiment currently preferred, the 11 epi PGF$_{2alpha}$-1-isopropyl ester is used.

Furthermore, the invention relates to compositions for the treatment of glaucoma or ocular hypertension, said compositions containing an effective intraocular pressure reducing amount of at least one 11 epi PGF$_{2alpha}$-1-ester defined as above, in an ophthalmologically compatible vehicle. The term "effective amount" here means that the composition contains about 0.1–10 µg, especially 1–10 µg of the active substance.

The ophthalmologically compatible vehicle which may be employed for preparing compositions of this invention comprises aqueous solutions as e.g. physiological salines, oil solutions or ointments. The vehicle furthermore may contain ophthalmologically compatible preservatives such as e.g. benzalkonium chloride, surfactants like e.g. Tween® 80, liposomes or polymers, for example methyl cellulose, polyvinyl alcohol, polyvinyl pyrrolidone and hyaluronic acid; these may be used for the purpose of increasing the viscosity. Furthermore, it is also possible to use soluble or insoluble drug inserts when the drug is to be administered.

The invention moreover relates to a method for treating glaucoma or ocular hypertension. The method consists in contacting a composition as aforesaid with the eye in order to reduce eye pressure and to maintain said pressure on a reduced level. The composition contains 0.1–10 µg, especially 1–10 µg, of the active substance i.e. the 11 epi PGF$_{2alpha}$ ester; the treatment may advantageously be carried out in that one drop of the composition, corresponding to about 30 µl, is administered about 1 to 4 times to the patient's eye.

The invention is illustrated by means of the following non-limitative examples.

EXPERIMENTS

1. Synthesis of 11 epi PGF$_{2alpha}$-1-isopropyl ester 20 mg (0.056 mmol) of 11 epi PGF$_{2alpha}$ (Cayman Chemicals, U.S.) were dissolved in acetone at room temperature. To this solution were added 54.5 mg (0.336 mmol) of diazabicycloundecene (DBu) and 76.15 mg (0.448 mmol) of propyl iodide, whereupon the mixture was left to stand at room temperature for 8 hours. The solvent was removed in vacuo, the residue then being dissolved in 50 ml of ethyl acetate, washed with 20 ml of water, 20 ml of 3% citric acid and 5% sodium hydrogen carbonate; thereafter the organic phase was dried over sodium sulfate. The solvent was removed in vacuo and the residue was purified by means of column chromatography on silica gel, with ethyl acetate-acetone (1:1) as the eluent. The yield of the product was about 76%, and its purity was tested by means of thin layer chromatography and NMR.

2. Preparation of eye drops containing 11 epi PGF$_{2alpha}$-1-isopropyl ester PGF$_{2alpha}$-1-isopropyl ester or 11 epi PGF$_{2alpha}$-1-isopropyl ester produced according to Example 1 was mixed with an eye drop solution containing 0.5% Tween 80 as a micelle-forming substance plus 0.01% benzalkonium chloride as a preservative to 50 µg/ml concentration. Healthy volunteers received in one of their eyes one drop (30 µl) containing 1.5 µg of either PGF$_{2alpha}$-1-isopropyl ester or 11 epi PGF$_{2alpha}$-1-isopropyl ester, and in the other eye one drop of the vehicle without any added prostaglandin compound, this other eye being the contralateral control eye. Feelings of irritation and hyperemia in the conjunctiva were then recorded during a period of two hours. Eye pressures were measured 2, 4, 6 and 8 hours after administration of 11 epi PGF$_{2alpha}$-1-isopropyl ester, and 4 and 8 hours after administration of PFG$_{2alpha}$-1-isopropyl ester. With prostaglandin eye drops the maximum pressure reducing effect in the eye is expected to be achieved 6–8 hours after administration of the preparation.

Eye pressure was measured by means of applanation tonometry, either with Godmann's applanation tonometer or with a pneumatonometer (Digilab Mode -30RT), after anesthesia of the cornea with oxybuprocaine drops or with a mixture of oxybuprocaine and fluorescein. Results could be read only after measurements were complete.

Feelings of irritation in the eye i.e. grittiness were classified by scores ranging from 0 to 3 where 0=no irritation, 1=slightly irritating, 2=moderately irritating and 3=highly irritating. Hyperemia in the conjunctiva was assessed only visually.

The results of the tests performed on healthy volunteers with 11 epi PGF$_{2alpha}$-1-isopropyl ester and PGF$_{2alpha}$-1-isopropyl ester are set forth in Tables I and II. Application of 1.5 µg of 11 epi PGF$_{2alpha}$ administered as the 1-isopropyl ester in a particular vehicle and application of 1.5 µg PGF$_{2alpha}$ administered as the 1-isopropyl ester in the same vehicle resulted in 1–2 mm Hg pressure reduction in normotensive individuals 4 to 8 hours after application, as compared to the control eye (Table I). The pressure reduction was statistically significant on a $P<0.05$ to $P<0.02$ level.

This pressure reduction may appear to be a small one, but it is a well-known fact that normotensive individuals will generally show fairly little reaction in response to pressure reducing drugs. This is true also of e.g. pilocarpine and timolol. As can be seen from Table II, irritation after application of 1.5 µg 11 epi PGF$_{2alpha}$ was felt to be considerably less than the irritation felt upon application of 1.5 µg PGF$_{2alpha}$ when each had been administered in the form of its 1-isopropyl ester. This is very important from a clinical point of view, since it may thus be espected that the drug will be used in doses high enough to bring about a maximal reduction of eye pressure.

REFERENCES

Bill, A (1975). Blood circulation and fluid dynamics in the eye. Physiol. Rev. 55: 383–417.

Crawford, K, Kaufman, P L, och True Gabel, B'A (1987). Pilocarpine antagonizes PGF$_{2a}$-induced ocular hypotension: Evidence for enhancement of uveoscleral outflow by PGF$_{2a}$. Invest. Ophthalmol. Vis Sci p. 11.

Liston, T och Roberts, L J (1985). Transformation of prostaglandin D$_2$ to 9alpha,11beta-(15S)-trihydroxyprosta-(5Z,13E)-dien-1-oic acid (9alpha,11beta-prostaglandin F$_2$): A unique biologically active prostaglandin produced enzymatically in vivo in humans. Proc Natl Acad Sci US 82 p. 6030–6034.

Nilsson, S F E, Stjernschantz, J, och Bill, A (1987). PGF$_{2a}$ increases uveoscleral outflow. Invest. Ophthalmol. Vis Sci Suppl p. 284.

Pugliese G et al (1985). Hepatic Transformation of Prostaglandin D$_2$ to a New Prostanoid, 9alpha,11beta-Prostaglandin F$_2$, That Inhibits Platelet Aggregation and Constricts Blood Vessels. J Biol Chem 260(27) p. 14621–14625.

TABLE 1

| Prostaglandin | n | 0 h Exp. (mmHg) | 0 h Contr. (mmHg) | 0 h Diff. (mmHg) | 2 h Exp. (mmHg) | 2 h Contr. (mmHg) | 2 h Diff. (mmHg) | 4 h Exp. (mmHg) | 4 h Contr. (mmHg) | 4 h Diff. (mmHg) |
|---|---|---|---|---|---|---|---|---|---|---|
| 11 epi PGF$_{2alpha}$-1-isopropyl ester | 5 | 14.7 ± 2.2 | 14.5 ± 1.6 | 0.3 ± 0.7 | 13.7 ± 2.0 | 15.1 ± 1.5 | −1.4 ± 0.7 | 13.4 ± 1.6 | 14.5 ± 1.4 | −1.1 ± 0.4[x] |
| PGF$_{2alpha}$-1-isopropyl ester | 6 | — | — | — | — | — | — | 15.6 ± 0.8 | 17.4 ± 1.3 | −1.8 ± 0.7[x] |

| Prostaglandin | 6 h Exp. (mmHg) | 6 h Contr. (mmHg) | 6 h Diff. (mmHg) | 8 h Exp. (mmHg) | 8 h Contr. (mmHg) | 8 h Diff. (mmHg) |
|---|---|---|---|---|---|---|
| 11 epi PGF$_{2alpha}$-1-isopropyl ester | 11.8 ± 2.0 | 13.8 ± 1.2 | −1.9 ± 1.1 | 12.1 ± 1.0 | 13.3 ± 1.0 | −1.2 ± 0.3[xx] |
| PGF$_{2alpha}$-1-isopropyl ester | — | — | — | 15.0 ± 0.4 | 16.9 ± 1.3 | −1.9 ± 1.1 |

Eye pressure reducing effect of 11 epi PGF$_{2alpha}$-1-isopropyl ester and PGF$_{2alpha}$-1-isopropyl ester on normotensive individuals after local application of a 30 μl eye drop containing 1.5 μg of the active substance calculated as free acid. Contralateral control eyes were treated with vehicle alone.
[x] $p > 0.05$
[xx] $p > 0.02$

TABLE II

| Prostaglandin | Time after application | | | | |
|---|---|---|---|---|---|
| | 15' | 30' | 45' | 60' | 120' |
| 11 epi-PGF$_{2alpha}$-1-isopropyl ester | 0.4 ± 0.2[xxx] | 0.2 ± 0.2[xxx] | 0.0 ± 0.0 | 0.0 ± 0.0 | 0.0 ± 0.0 |
| PGF$_{2alpha}$-1-isopropyl ester | 1.5 ± 0.4 | 1.7 ± 0.2 | 1.8 ± 0.2 | 1.3 ± 0.2 | 0.5 ± 0.2 |

[xxx] $p < 0.01$

Feeling of pain (grittiness) in the eye of normotensive individuals after local application of 1.5 μg 11 epi PGF$_{2alpha}$-1-isopropyl ester or 1.5 μg PGF$_{2alpha}$-1-isopropyl ester calculated as free acid. A scale of scores ranging from 0 to 3 was used for pain assessment.

We claim:

1. A method for the treatment of glaucoma or ocular hypertension which comprises contacting the eye with a composition containing an ophthalmologically compatible vehicle and an effective intraocular pressure reducing amount of a compound selected from the group consisting of
   (a) 11 epi PGF$_{2alpha}$-1-alkyl ester and
   (b) 11 epi PGF$_{2alpha}$-1-alkylaryl ester.

2. A method according to claim 1 wherein the alkyl chain in (a) has 1-10 carbon atoms.

3. A method according to claim 1 wherein the alkyl chain in (a) has 1-7 carbon atoms.

4. A method according to claim 1 wherein the alkyl chain in (a) has 1-5 carbon atoms.

5. A method according to claim 1 wherein in (b) the aryl group is monosubstituted by a lower alkyl group having 1-5 carbon atoms.

6. A method according to claim 1 wherein (a) is 11 epi PGF$_{2alpha}$-1-isopropyl ester.

7. A composition for the treatment of glaucoma or ocular hypertension which comprises an ophthalmologically compatible vehicle and an effective intraocular pressure reducing amount of a compound selected from the group consisting of
   (a) 11 epi PGF$_{2alpha}$-1-alkyl ester and
   (b) 11 epi PGF$_{2alpha}$-1-alkylaryl ester.

8. A composition according to claim 7 wherein the alkyl chain in (a) has 1-10 carbon atoms.

9. A composition according to claim 7 wherein the alkyl chain in (a) has 1-7 carbon atoms.

10. A composition according to claim 7 wherein the alkyl chain in (a) has 1-5 carbon atoms.

11. A composition according to claim 7 wherein in (b) the aryl group is monosubstituted by a lower alkyl group having 1-5 carbon atoms.

12. A composition according to claim 7 wherein (a) is 11 epi PGF$_{2alpha}$-1-isopropyl ester.

* * * * *